United States Patent [19]

Sleezer et al.

[11] 3,996,236
[45] Dec. 7, 1976

[54] METHOXYMETHYL D-6-(2,2-DIMETHYL-5-OXO-4-PHENYL-1-IMIDAZOLIDINYL)PENICILLANATE

[75] Inventors: Paul D. Sleezer, Dewitt; David A. Johnson, Fayetteville, both of N.Y.

[73] Assignee: Bristol-Myers Company, New York, N.Y.

[22] Filed: Feb. 18, 1975

[21] Appl. No.: 550,317

Related U.S. Application Data

[63] Continuation-in-part of Ser. No. 341,196, March 24, 1973, abandoned, which is a continuation-in-part of Ser. No. 180,070, Sept. 13, 1971, abandoned.

[52] U.S. Cl. .................... 260/306.7 C; 260/239.1
[51] Int. Cl.$^2$ .................................... C07D 499/02
[58] Field of Search ................ 260/306.7 C, 239.1

[56] References Cited

UNITED STATES PATENTS

| 3,198,804 | 8/1965 | Johnson et al. | 260/239.1 |
| 3,652,546 | 3/1972 | Cheney et al. | 260/239.1 |
| 3,864,332 | 2/1975 | Rabinovich et al. | 260/239.1 |

FOREIGN PATENTS OR APPLICATIONS

| 1,217,143 | 12/1970 | United Kingdom | 260/239.1 |

OTHER PUBLICATIONS

Jansen et al., J. Chem. Soc., pp. 2127–2132 (1965).
Jackson et al., Chem. Comm., pp. 14–15 (1970).

*Primary Examiner*—Gerald A. Schwartz
*Attorney, Agent, or Firm*—Herbert W. Taylor, Jr.

[57] ABSTRACT

The specification discloses a process for preparing methoxymethyl D-6-(2,2-dimethyl-5-oxo-4-phenyl-1-imidazolidinyl)penicillanate and the use of this compound as a well absorbed antibacterial agent and also as an intermediate in the preparation of other antibiotic derivatives of 6-aminopenicillanic acid such as hetacillin. The methoxymethyl ester of ampicillin is also disclosed.

2 Claims, No Drawings

METHOXYMETHYL D-6-(2,2-DIMETHYL-5-OXO-4-PHENYL-1-IMIDAZOLIDINYL)PENICILLANATE

CROSS-REFERENCE TO RELATED APPLICATIONS

This application is a continuation-in-part of our prior, copending U.S. application Ser. No. 341,196 filed Mar. 24, 1973 and now abandoned, which was in turn a continuation-in-part of our prior, copending U.S. application Ser. No. 180,070 filed Sept. 13, 1971 and now abandoned.

BACKGROUND OF THE INVENTION

1. Field of the Invention.

The antibiotic compound of this invention is a derivative of hetacillin and is thus a member of the penicillin group of chemicals.

2. Description of the Prior Art.

Esters of benzylpenicillins are disclosed in British Pat. No. 1,003,479 and U. S. Pat. No. 2,650,218, acyloxymethyl esters of ampicillin are discussed by W. v. Daehne et al. in J. Med. Chem., 13, (4), 607-612 (1970). This publication also refers to early publications on the hydrolysis of esters. The pivaloyloxymethyl ester of ampicillin is also disclosed in U.S. Pats. Nos. 3,660,575 and 3,697,507. Various penicillin esters are also disclosed, for example, in U.S. Pat. No. 3,528,965 and U.K. Pat. No. 1,267,936. Various esters of 6-aminopenicillanic acid have been disclosed, for example, in U.S. Pat. Nos. 3,652,546 and 3,399,207. The crystalline toluene-p-sulphonate of the methoxymethyl ester of 6-aminopenicillanic acid was described by Jackson et al., Chemical Communications, 1970, pages 14-15. Methoxymethyl benzylpenicillinate and other penicillin esters are described by Jansen et al., J. Chem. Soc., 2127-32 (1965) and that publication refers to earlier publications such as Johnson, J. Amer. Chem. Soc., 75, 3636 (1953) and Barnden et al., J. Chem. Soc., 3733 (1953). The Jansen et al. publication is referred to in U.K. Pat. No. 1,217,143 published Dec. 31, 1970 (but not in the corresponding U. S. Pat. No. 2,650,218) in its generic disclosure on page 2 which names various specific esters of penicillins, including methoxymethyl, and suggests acylation of those and other esters of 6-aminopenicillanic acid (6-APA) with "any of the acyl groups found in the side chains of known antibacterial penicillins, especially the group of" the formula for D-(−)-2-phenylglycine which occurs in ampicillin.

Subsequent to the filing on Sept. 13, 1971 of the parent of this application in the U.S. there appeared abroad applications corresponding to said parent application U.S. Ser. No. 180,070 as exemplified by Belgium 788,720 to Bristol-Myers Company reported and abstracted as Farmdoc 18226U by Derwent Publications Ltd, Rochdale House, 128 Theobalds Road, London WCLX 8RP, England, in the issue of Central Patents Index - Basic Abstracts Journal - B - Farmdoc dated May 17, 1973. In the issue of Feb. 8, 1973 Bel. Pat. No. 784,800 to Yamanouchi Pharmaceutical Co., Ltd. was abstracted as Farmdoc 81300T; this Belgian patent generically claims, inter alia, compounds of the formula

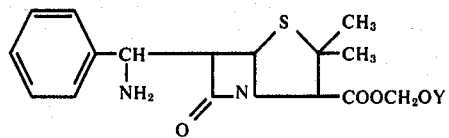

wherein Y is, inter alia, lower alkyl and also contains working examples wherein Y is ethyl and some higher homologs and contains on page 4 a reference to the use of chloromethyl methyl ether (Y equals methyl).

Hetacillin is a penicillin derivative known, in the acid form, as D-6-(2,2-dimethyl-5-oxo-4-phenyl-1-imidazolidinyl)penicillanic acid. This compound, i.e., hetacillin, and many closely related compounds and the preparation thereof are disclosed in U. S. Pat. No. 3,198,804.

SUMMARY OF THE INVENTION

This invention is directed to the preparation of methoxymethyl hetacillin which is the acetoneadduct of the methoxymethyl ester of ampicillin. The term acetone-adduct refers to the product obtained by reacting the appropriate α-amino compound with a stochiometric amount of acetone to obtain the product described by structure I below. Moreover, this invention contemplates the use of this ester as an intermediate in the synthesis of other semisynthetic penicillin antibiotics.

The methoxymethyl hetacillin of this invention is characterized by the following structure:

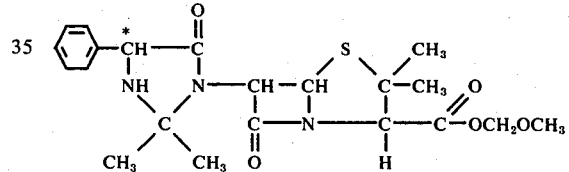

having the D-configuration at the carbon atom marked with an asterisk.

In general, the methoxymethyl ester of hetacillin can be prepared by reacting the antibiotic with a suitable esterifying derivative of dimethyl ether, such as a halomethyl methyl ether. The ester can also be prepared from a basic fermentation-produced penicillin, such as phenoxymethyl penicillin by a series of reactions in which the phenoxymethyl-penicillin ester is deacylated by known procedures to provide the corresponding methoxymethyl ester of 6-aminopenicillanic acid. The 6-APA ester and a suitable acylation agent can then be reacted as shown herein.

The 6-APA ester can be acylated by known procedures to provide various penicillin esters according to the choice of acylating agents. The choice of acylating agent and conditions for acylation are not narrowly critical. Either the free acid, that is, D-(−)-2-phenylglycine, or its equivalent can be employed to acylate the free amino group of the 6-APA ester. Such acylating agents include the free acid and the corresponding carboxylic acid halides, e.g., the chlorides and bromides; the acid anhydrides, including mixed anhydrides and particularly the mixed anhydrides prepared from acids such as the lower aliphatic monoesters of carbonic acid, of alkyl and aryl sulfonic acid and of more hindered acids, such as diphenylacetic acid. In addition, an acid azide or an active ester of thioester (e.g., with p-nitrophenol, 2,4-dinitrophenol, thiophenol, thioacetic acid) may be used or the free acid itself may be coupled with 6- aminopenicillanic ester after first reacting said free acid with N,N'-dimethylchloroformiminium chloride [cf. Great Britain 1,008,170 and Novak and Weichet, Experientia XXI/6, 360 (1965)] or by the use of enzymes or of an N,N'-carbonyldiimidazole or an N,N'-carbonylditriazole [cf. South African Patent Specification 63/2684] or of a carbodiimide reagent [especially N,N'-dicyclohexylcarbodiimide, N,N'-diisopropylcarbodiimide or N-cyclohexyl-N'-(2-morpholinoethyl) carbodiimide; cf. Sheehan and Hess, J. Amer. Chem. Soc., 77, 1067 (1955)], or of alkynylamine reagent [cf. R. Buijle and H. G. Viehe, Angew. Chem. International Edition, 3, 582 (1964)], or of a ketenimine reagent [cf. C. L. Stevens and M. E. Monk, J. Amer. Chem. Soc. 80, 4065 (1958)] or of an isoxazolium salt reagent [cf. R. B. Woodward, R. A. Olofson and H. Mayer, J. Amer. Chem. Soc., 83, 1010 (1961)] or of hexachlorocyclotriphosphatriazine or hexabromocyclotriphosphatriazine (U.S. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)] and it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc. 90, 823–824 and 1652–1653 (1968). Another equivalent of the acid is a corresponding azolide, i.e., an amide of the acid the amide nitrogen of which is a member of a quasi-aromatic five-membered ring containing at least two nitrogen atoms, i.e., imidazole, pyrazole, the triazoles, benzimidazole, benzotriazole, and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolides. The by-product, imidazole, precipitates and may be separated and the imidazolide isolated, but this is not essential. The methods for carrying out these reactions to produce a penicillin and the methods used to isolate the penicillin so produced are well known in the art (cf. U.S. Pat. Nos. 3,079,314, 3,117,126, 3,129,224 and British Pat. Nos. 932,644, 957,570 and 959,054).

Mention was made above of the use of enzymes to couple the free acid with methoxymethyl 6-aminopenicillanate. Included in the scope of such processes are the use of an ester, e.g. the methyl ester, of that free acid with enzymes provided by various microorganisms, e.g. those described by T. Takahashi et al., J. Amer. Chem. Soc. 94(11), 4035–4037 (1972) and by T. Nara et al., J. Antibiotics (Japan), 24(5), 321–323 (1971) and in U.S. Pat. No. 3,682,777.

In a case such as this where the acylating agent contains a free amino group, it may be desirable to protect it with a suitable blocking agent. Such protecting groups include those of the general formula ROCO— in which R is an allyl, benzyl, substituted benzyl, phenyl, substituted phenyl, or trityl group. It is usually preferred, however, to use D-(−)-2-phenylglycyl chloride hydrochloride as the acylating agent.

Another preferred process consists of a) acylating the methoxymethyl ester of 6-aminopenicillanic acid with an acid in the D- configuration of the formula

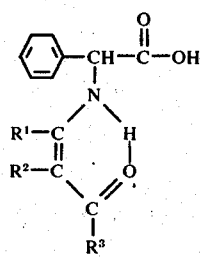

wherein $R^1$ is alkyl, aralkyl or aryl, $R^2$ is hydrogen, alkyl, aralkyl or aryl and $R^3$ is alkyl, aralkyl, aryl, alkoxy, aralkoxy, aryloxy or

wherein $R^4$ and $R^5$ are each hydrogen, alkyl, aralkyl or aryl or, when taken together with the nitrogen atom, are piperidino or morpholino, or an acylating derivative thereof in an inert solvent at a temperature below 0° C., and (b) removing the α-amino-protecting group.

In this process it is preferred that there is also present during step (a) a compound of the formula

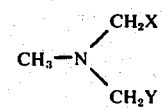

wherein X is a hydrogen atom or an alkyl or phenyl group, Y is a hydrogen atom or a lower alkyl group, or X and Y together represent any one of the divalent radicals, ethylene, substituted ethylene, trimethylene, —CH₂OCH₂— or —CH₂N(CH₃)CH₂—. Examples of such catalysts are N-methylmorpholine and N,N-dimethylbenzylamine. It is preferred that the inert solvent be acetone or aqueous acetone or tetrahydrofuran and that the acylating derivative be a mixed anhydride formed from an alkyl chlorocarbonate.

It is further preferred that, in the en-amine aminoprotecting group, $R^1$ is methyl, $R^2$ is hydrogen and $R^3$ is methoxy, ethoxy or methyl; this requires the use of methyl acetoacetate, ethyl acetoacetate or acetylacetone.

In the removal of the α-amino-protecting group it is preferred that use be made of a strong mineral acid such as hydrochloric acid or of formic acid.

The resulting penicillin ester, e.g., the methoxymethyl ester of ampicillin, can be reacted with acetone to form the acetone adduct ester, e.g., hetacillin ester, in accordance with the procedure disclosed in the U.S. Pat. No. 3,198,804.

Broadly, this process involves esterification of a natural penicillin of the structure

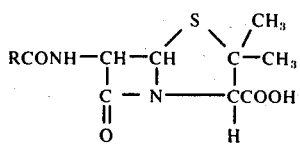

wherein R is an organic radical of which many are well known in the penicillin art. The acyl group of any of the well known natural penicillins can be employed. A particularly suitable side chain is the phenoxymethyl group.

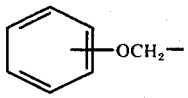

Illustrative organic radicals include benzyl, furylmethyl, thienylmethyl and the like. As is well known, the various organic radicals can be substituted.

More particularly, in the process of this invention a salt of phenoxymethyl penicillin in a suitable reaction medium is reacted with chloromethyl methyl ether or bromomethyl methyl ether at a temperature between about 0° C. and 50° C. and preferably between 0° C. and about 30° C. A preferred reaction medium is methylene chloride to which may be added some dimethylformamide generally in a ratio of about 1 to 2 ml. per 150 ml. of methylene chloride. Dimethylformamide can also be used as a reaction medium. The reaction product can be recovered by conventional methods.

The recovered ester of phenoxymethyl penicillin is then deacylated, either enzymatically or chemically. Enzymatic production of 6-APA by deacylation of a penicillin is disclosed in U.S. Pat. No. 3,014,846. The preferred method of chemical cleavage is carried out by forming an imino halide by reaction with a halogenating agent, such as phosphorous pentachloride. The ester is dissolved in a non-aqeous solvent, such as methylene chloride, benzene or chloroform, to which there has been added a suitable amount of an acid-binding agent, such as dimethylaniline, pyridine, quinoline, or lutidine. The amount of acid-binding agent should be sufficient to take up the acid formed by the cleavage reaction. The chlorination reaction temperature should be maintained between about −50° C. to about 0° C. to provide complete chlorination of the ester. The imino chloride is then treated with an alcohol under acid conditions whereby an imino ether is formed under anhydrous conditions. Water is then added to the reaction mixture to hydrolyze the ether. The imino ether can conveniently be formed at temperatures of from about −70° C. to about −30° C.

The general procedure for this series of reactions is disclosed in U.S. Pat. No. 3,499,909 along with various halogenating agents, acid-binding agents, alcohols, and solvents all of which are generally applicable to the herein disclosed methoxymethyl esters. Thus, the 6-APA ester can be isolated from the reaction mixture as the free base or as an acid addition salt such as the p-toluene-sulfonate salt.

Acylation of the 6-APA ester to provide the methoxymethyl ester of ampicillin can be achieved following known procedures, such as those disclosed in U.S. Pat. No. 2,985,648 and 3,140,282.

The p-toluene-sulfonate salt of the methoxymethyl ester of 6-APA is then contacted with an acylating agent, such as D-(−)-2-phenylglycyl chloride hydrochloride, in either anhydrous methylene chloride or in acidic aqueous medium at low temperature. Broadly, the acylating agent is employed in amounts of about 1 to 3 moles per mole of 6-APA ester, and the temperature should be between about −10° C. and +20° C. The pH of the reaction medium should be below 4 and preferably from about 1.5 to about 3.0, usually between 2.0 and 2.8. The reaction medium is often a mixture of water and organic solvents such as acetone, methylene chloride, or tetrahydrofuran.

Any solids are removed by filtration to provide a solution of the ampicillin ester. The acylated ester is recovered by raising the pH of the reaction medium to about 4 or above, e.g., between 4 and 7.

In a preferred procedure, the ester is dissolved in methylene chloride-acetone mixture at ice bath temperatures generally between about 0° C. and 5° C. A small amount of water, about 2.5 percent based on the volume of the organic solvent, is then added, preferably in about stochiometric amounts. The resulting admixture is maintained at about 0° C. until the acid chloride has dissolved. The reaction product can then be recovered by standard methods. This reaction can be run under anhydrous conditions.

Alternatively, the 6-APA ester can be prepared directly from 6-aminopenicillanic acid by a process in which 6-APA is slurried at about 25° C. in methylene chloride and dissolved therein as the triethylamine salt. The reaction mixture is then cooled to about 0° C. and esterified with chloromethyl methyl ether. The 6-APA ester can be isolated from the reaction mixture as the free base or as an acid addition salt. The p-toluene-sulfonate salt of the 6-APA ester has been described in the literature by Jackson et al., Chemical Communications, 14, 1970.

The ampicillin methoxymethyl ester can be converted to the corresponding hetacillin ester in reaction with aqueous acetone at a pH of from about 6.5 to about 9.5. In general, this step of the process can be carried out at a temperature between about −10° C. and 15° C., although it is generally preferred to employ temperatures of about 0° C. to about 5° C. The pH and temperature should be maintained for a period of time which is sufficient to provide substantial conversion to hetacillin, e.g., from about 12 to 170 hours, depending on the other conditions. After the reaction period, the hetacillin methoxymethyl ester can be recovered by adjusting the pH of the reaction mixture to between 1.5 and 2.0 with an acid such as hydrochloric acid and extracting with a suitable solvent such as methylene chloride. The hetacillin ester is recovered from the organic phase in the usual manner.

The hetacillin ester can be conveniently converted to hetacillin by hydrolysis of the ester group under acidic or mildly alkaline conditions. The ester can be hydrolyzed in hydrochloric acid having a strength of from 1 to 6 normal at temperatures between about 0° C. and 40° C. In concentrated hydrochloric acid, the product is recovered as a hydrochloride salt which can easily be redissolved in a suitable solvent, such as water or a mixture of water and an organic liquid, such as acetone or methyl isobutyl ketone, and then reprecipitated by bringing the pH to the isoelectric point for hetacillin-free acid, i.e., about 2.5. Precipitation of the hydrochloride salt can be aided by the use of suitable solute, such as ammonium chloride.

The following examples are given in illustration of, but not in limitation of, the present invention. All temperatures are in degrees Centigrade. Methyl isobutyl ketone is represented as MIBK.

LA-1 resin is a commercially available mixture of secondary amines wherein each secondary amine has the formula

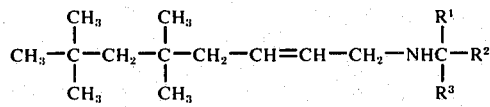

wherein each of $R^1$, $R^2$ and $R^3$ is a monovalent aliphatic hydrocarbon radical and wherein $R^1$, $R^2$ and $R^3$ contain in the aggregate from eleven to fourteen carbon atoms. This particular mixture of secondary amines, which is sometimes referred to as "Liquid Amine Mixture No. I", is a clear amber liquid having the following physical characteristics: molecular weight of 351–393; freezing point below −80° C; neutralization equivalent of 380–410; acid binding capacity of 2.5 − 2.7 meq./gm.; viscosity at 25° C. of 72 cps.; specific gravity at 25° C. of 0.84; % (volume) distilled at 10 mm. below 160° C. + 5% maximum; 50% (volume) distillation point at 10 mm. = 210° C.

DESCRIPTION OF THE PREFERRED EMBODIMENTS

EXAMPLE 1

Methoxymethyl Ester of Penicillin V.

Potassium phenoxymethylpenicillinate (38.8 grams) was slurried in 150 ml. of methylene chloride and the mixture cooled to about 5° C. by means of a cooling bath, and 9.5 grams (0.118 mole) of chloromethyl methyl ether and 0.5 ml. of dimethylformamide was added. The cooling bath was removed and the mixture stirred for about 1.5 hours while allowing the mixture to come to room temperature. The methylene chloride solution was washed four times with 200 ml. portions of water and then dried and stripped of solvent by distillation in vacuo to give 33.5 grams of methoxymethyl ester of penicillin V as a yellowish oil. The yield was about 84%.

EXAMPLE 2

Preparation of Pen V Methoxymethyl Ester

To 100 g. (0.257 mole) of K Pen V (potassium phenoxymethylpenicillin) slurried in 300 ml. of dry dichloromethane and cooled to 0°-5° C. was added over about 10 min., 32.12 g. (0.257 mole) of bromomethyl methyl ether in 60 ml. dichloromethane. After the addition, 1 ml. of DMF (dimethylformamide) was added and the reaction was allowed to proceed 3 hr. at 0°-5° C. TLC (thin layer chromatography) (50/50 acetone/benzene) showed a major zone for product, Rf about 0.7.

The reaction mixture was washed with 3 × 100 ml. portions of water, dried over MgSO₄ and concentrated under reduced pressure at about 40° to an oil. The oil was taken up in 300 ml. of 2-propanol at about 25°, seeded and crystallized 12 hr. at 0-5°. The white crystals were collected by filtration and washed with 2-propanol, followed by heptane, and gave after drying at about 25° in a vacuum oven for about 4 hr. 68 g. (about 67% yield) of Pen V methoxymethyl ester homogeneous on TLC and showing consistent and clean ir and nmr spectra.

EXAMPLE 3

6-APA Methoxymethyl Ester as its p-Toluenesulfonate.

To 57 g. (0.145 mole) of Pen V methoxymethyl ester dissolved in 500 ml. CH₂Cl₂ and cooled to −30° C. was added 37 ml. of N,N-dimethylaniline, followed by 33.1 g. of phosphorous pentachloride. The mixture was stirred at −30° C.) for 90 min. TLC showed almost no residual methoxymethyl ester of Pen V. The mixture was cooled to about −60° C. and 150 ml. of precooled (−50° C.) methanol was added in one portion. The temperature was then held at about −40° C. for 2 hours. The solution was then added rapidly to 150 ml. of 0-5° water and held for 10 min. at 0° to 5° C. The pH was about 0.8.

Maintaining this temperature range, 10% NaOH solution was used to adjust to pH 6.9. The layers were separated and the dichloromethane layer washed with 3 × 100 ml. portions of cold water. After drying over magnesium sulfate, the CH₂Cl₂ layer was concentrated under vacuum to about half volume and 54 g. (0.284 mole) of p-toluenesulfonic acid dissolved in 120 ml. of acetone was added. Seed crystals of product were added and the mixture crystallized at 0° to 5° C. for 2 hr. After collecting by filtration, washing with 100 ml. of 50/50 CH₂Cl₂/heptane and drying in a circulating air oven at about 30° C. for 4–6 hr., there was obtained 23.7 g. (37.8% yield) of the p-toluenesulfonic acid salt of 6-APA methoxymethyl ester.

EXAMPLE 4

6-Aminopenicillanic Acid Methoxymethyl Ester.

To a solution of 12 grams (0.0304 mole) of penicillin V methoxymethyl ester in 100 ml. of methylene chloride cooled to −55° C., there was added 4.8 ml. (4.6 grams, 0.038 mole) of dimethylaniline and this followed directly by 7.0 grams (0.0337 mole) of phosphorous pentachloride dissolved in 100 ml. of methylene chloride.

The mixture was held at −40° C. to −50° C. for about 2 hours. Thin layer chromatography indicated complete chlorination of the pen V ester. The mixture was then cooled to −70° C. and 47 ml. of methanol, precooled to −50° C., was added rapidly. The mixture was then held for 2 hours at −50° C. to −40° C. To the resulting yellow solution, 100 ml. of water was added with vigorous agitation. The temperature of the reaction mixture rose to about 0° C., and the pH of the mixture was about 0.6 to 1.0. After holding the mixture for about 10 to 15 minutes at this temperature and pH range, the pH was brought to 6.5 to 6.8 with dilute sodium hydroxide. The layers were separated and the methylene chloride layer was washed with water, carbon treated, and dried to yield the desired methoxymethyl 6-aminopenicillanate. Thin layer chromatography showed that this solution contained dimethylaniline, methyl phenoxyacetate, and 6-APA methoxymethyl ester.

EXAMPLE 5

Methoxymethyl D-α-Aminobenzylpenicillinate.

A methylene chloride solution containing methoxymethyl ester of 6aminopenicillanic acid prepared from 0.04 mole of methoxymethyl phenoxymethylpenicillinate as in Example 2 was diluted with 100 ml. of acetone. After cooling the resulting mixture to about 0° C. to 5° C., 5 ml. of water and 0.04 mole (4.8 grams) of dimethylaniline was added to the solution. Eight grams (0.039 mole) of D-2-phenylglycyl chloride hydrochloride was then added to the solution with vigorous stirring. The mixture was stirred for about one hour at 0° C. by which time all the acid chloride had dissolved. The yield of methoxymethyl ester of D-α-aminobenzylpenicillin was 42%, as determined by bioassay of the reaction product mixture.

EXAMPLE 6

Methoxymethyl Ester of Hetacillin

An acylation reaction, as described in Example 5 was carried out using 13.0 grams (0.05 mole) of 6-aminopenicillanic acid ester and 20.6 grams (0.10 mole) of D-(−)-2-phenylglycyl chloride hydrochloride. After filtering off any undissolved phenylglycyl chloride hydrochloride, the pH of the solution was adjusted to 8.5 with 10% sodium hydroxide and the mixture aged at 8° C. for about 90 hours. Bioassay showed a yield of about 60%. The pH of the aged mixture was then adjusted to 1.8 with 6 N hydrochloric acid and the mixture extracted with methylene chloride. The methylene chloride layer was washed with water, dried and stripped to yield about 14.4 grams of product.

EXAMPLE 7

Hetacillin.

a. Five grams of methoxymethyl ester of hetacillin was slurried in 50 ml. of 3 N hydrochloric acid at 25° C. for about 20 minutes with vigorous stirring. The mixture was cooled by a water bath to about 0° C. to 5° C., and the pH was adjusted to 3.1 with 20% sodium hydroxide. After crystallization, the solid was separated by filtration and washed with acetone. The yield was 2.05 grams of hetacillin having a potency of 913 mcg./mg.

b. Hetacillin methoxymethyl ester, one gram, was added to 20 ml. of 6 N HCl stirred for two minutes, seeded with hetacillin hydrochloride crystals and cooled to 0° C. to 5° C. After about 10 minutes of additional crystallization, hetacillin hydrochloride was filtered off. The yield was 64% of material with spectral properties (IR and NMR) and TLC comparable to hetacillin hydrochloride.

EXAMPLE 8

Hetacillin Methoxymethyl Ester

To 38.9 grams (0.1 mole) of hetacillin in 200 ml. of dry methylene chloride at 25° C. was added 10.1 grams (0.1 mole) of triethylamine. The clear solution was cooled to 0° C. and 8.05 grams (8 ml., 0.1 mole) of chloromethyl methyl ether dissolved in 50 ml. of methylene chloride was added over 10 minutes. After stirring 1 hour at 0° C., the reaction mixture was polish filtered and concentrated under reduced pressure to an oil which was taken up in acetone, polish filtered and again concentrated to an oil. This oil was taken up in methylene chloride and washed with water at pH 2 then twice with water at pH 7. After drying, the methylene chloride was removed under vacuum to give an amorphous, frothy solid, 40 grams or 93% yield. This material was homogeneous on TLC, and IR and NMR spectra were consistent with structure of the desired product.

A 2.0 gram (4.6 mmoles) sample was dissolved in 25 ml. acetone, and 0.75 gram (6.3 mmoles) of p-toluenesulfonic acid monohydrate was added to the solution. On adding 25 ml. of diethyl ether, crystallization started. After 15 minutes at 0° C., the white crystals were filtered and washed with ether and dried to yield 1.9 grams of the toluenesulphonate salt of hetacillin methoxymethyl ester.

$C_{28}H_{35}N_3S_2O_8$ Calculated: C: 55.45; H: 5.82; N: 6.92. Found: C: 55.75; H. 6.12; N: 6.92.

In a similar preparation, 20 grams (0.046 mole) of hetacillin ester was stirred in 70 ml. of tetrahydrofuran and 3 ml. of concentrated hydrochloric acid at 25° C. for 20 minutes and then at 0° C. to 5° C. for 30 minutes. The resulting white precipitate was filtered and washed with 100 ml. of acetone in portions. There was obtained 16 grams of white crystalline hetacillin ester hydrochloride. Spectra were consistent with the desired structure. Bioassay showed activity of 764 mcg/mg vs. hetacillin.

$C_{21}H_{28}N_3O_5HCl$. Calculated: C: 53.65; H: 6.00; N: 8.94; Cl 7.54. Found: C: 53.44; H: 5.95; N: 8.74; Cl: 7.72.

EXAMPLE 9

Acylation of p-toluenesulfonate Salt of Methoxymethyl 6-aminopenicillanate.

Three millimoles (1.3 grams) of p-toluenesulfonate salt of methoxymethyl 6-aminopenicillanate was admixed with 40 ml. of acetone and 10 ml. of water. The mixture was cooled to between 0° C. and 5° C. To the cooled mixture there was added six millimoles (1.2 grams) of phenylglycyl chloride hydrochloride with virgorous stirring. The pH of the reaction mixture was maintained between 2.0 and 2.8 by addition of 10% sodium hydroxide, as needed. After the reaction was complete, the pH was adjusted to between 6.5 and 7.0 and the mixture was filtered and diluted to 200 ml. with acetone to give a solution of the methoxymethyl ester of ampicillin.

EXAMPLE 10

Ampicillin Methoxymethyl Ester Hydrochloride.

At 25° C. in 150 ml. of dimethylacetamide there was dissolved 37.1 grams (0.1 mole) of sodium ampicillin. The solution was cooled to 0° C. to 5° C. and 8.0 ml. (0.1 mole) of chloromethylmethyl ether added. After one hour of stirring, thin-layer chromotography showed no sodium ampicillin remaining. The mixture was poured into 200 ml. of cold pH 7 buffer and extracted three times with 100 ml. portions of methylene chloride. The methylene chloride extracts were added to about 150 ml. cold water and the pH adjusted to 1.6 with hydrochloric acid. The water layer was separated and adjusted to pH 6.8 with dilute sodium hydroxide and extracted three times with 100 ml. portions of methylene chloride. The methylene chloride layers were dried over sodium sulfate and concentrated under reduced pressure to give a colorless oil showing one zone on thin-layer chromatogram. The oil was dissolved in 2-propanol, cooled, and HCl in 2-propanol added. This solution was then added to 700 ml. of cold, well-stirred ether. A white ppt. was formed which after 15 minutes of stirring was filtered and washed with cold ether. There was obtained 12 grams of white solid soluble in water. IR and NMR spectra were consistent with structure for the hydrochloride salt of the methoxymethyl ester of ampicillin. Bio potency as ampicillin showed activity of 682 mcg/mg.

A useful embodiment of the process of this invention is a continuous series of reactions carried out without isolation or recovery of intermediates. For example, the potassium salt of phenoxymethylpenicillin is esterified with chloromethylmethyl ether in methylene chloride at a temperature between 0° C. and 30° C. The methylene chloride solution of the ester is then successively treated with phosphorous pentachloride, methyl alcohol, and water to complete removal of the phenoxymethyl side chain and provide a methylene chloride solution containing the methoxymethyl ester of 6-APA. This solution is then carried forward and used in the acylation reaction in which D-(−)-2-phenylglycyl chloride hydrochloride is added to the solution to give a methylene chloride solution of the ampicillin ester. In the final step, the solution of ampicillin ester is treated with acetone at pH 7.5 to 8.5 and held until hetacillin ester formation has proceeded. Hetacillin itself is recovered from the organic phase by treatment thereof with a strong acid and water, e.g., three normal hydrochloric acid. The hetacillin is insoluble in the liquid phase and crystallizes.

Oral absorption of the hetacillin ester was evaluated and compared to ampicillin and hetacillin, as shown in Table I, following. In each case, the antibiotic was administered orally in equivalent amounts to a group of eight male mice. The blood levels were determined by plate assay on *Bacillus substilus* and reported as micrograms per milliliter of ampicillin.

The data indicate that the hetacillin ester in mice is more rapidly absorbed into the mouse blood than either hetacillin or ampicillin, thus providing for early attainment of peak levels of the antibiotic in the blood.

TABLE I

Blood Levels after Oral Administration to Mice

| Compound | Dose (mg./kg.) | Blood Levels (μg/ml) | | | |
|---|---|---|---|---|---|
| | | 0.5 | 1 | 2 | 3.5 |
| | | Hours after Administration | | | |
| Ester[1] | 126 | 8.49 | 3.49 | 1.43 | 0.42 |
| Hetacillin[1] | 115 | 4.30 | 5.00 | 2.10 | 0.38 |
| Ampicillin[1] | 100 | 5.79 | 5.34 | 1.91 | 0.44 |
| Ester[2] | 126 | 10.20 | 4.48 | 1.53 | 0.42 |
| Ampicillin[2] | 100 | 5.35 | 3.67 | 1.45 | 0.51 |
| Hetacillin[2] | 115 | 2.52 | 2.81 | 1.46 | 0.52 |

[1]Administered in 5% sodium bicarbonate
[2]Administered in distilled water

Excretion and additional absorption data were obtained from studies on rat urine shown in Table II, below. The compounds were administered in 0.0001 m. phosphate buffer, and the amount of antibiotic recovered reported as ampicillin.

TABLE II

Urinary Recovery of Methoxymethyl Ester of Hetacillin After Oral Administration to Rats

| Compound | Dose (mg/kg) | No. of Animals | Percent Recovered Hours After Administration | | |
|---|---|---|---|---|---|
| | | | 0–6 | 6–24 | 0–24 |
| Ester | 63 | 5 | 17.09 | 0.56 | 17.65 |
| Hetacillin | 57.5 | 5 | 4.42 | 0.52 | 4.94 |
| Ampicillin | 50 | 5 | 6.13 | 0.36 | 6.49 |

A rapid appearance of antibiotic in the urine indicates a suitability for treatment of urinary tract infections.

In addition to being a useful intermediate in a process for preparing hetacillin, the methoxymethyl ester of hetacillin has significant antibiotic properties. This compound also has value as an antibiotic because of its ability to give more rapid peak blood serum levels as compared to sodium ampicillin. When tested in beagle dogs, the methoxymethyl ester of hetacillin was found to give peak blood levels about 15 to 20 minutes after administration. Peak levels for sodium ampicillin occur about one hour after administration under comparable conditions.

One of the factors in antibiotic evaluation is the biological half-life of the antibiotic. In beagle dogs, the methoxymethyl ester of hetacillin was found to have a half-life of about 1.2 hours. Under comparable conditions, sodium ampicillin was found to have a half-life of only 30 to 40 minutes. In these tests, the concentration of antibiotic was measured by bioassay.

Further studies have indicated that the methoxymethyl ester of hetacillin is more favorably distributed throughout the body tissue. Tests carried out in beagle dogs have shown that the ester has a significantly higher apparent volume of distribution, i.e., the drug seems to be dissolved in a larger fluid volume, as compared to sodium ampicillin.

The absorption, distribution, and excretion characteristics of the methoxymethyl ester of hetacillin in beagle dogs gives this compound a unique pharmacokinetic profile which has not been previously reported for any penicillin. The compound is extensively distributed to the various organs and tissues of the body. The volume of distribution has been calculated at approximately 85% of the total body volume as compared to about 25% for sodium ampicillin. These distribution characteristics result in a significant prolongation of plasma and urinary excretion half-life values. For example, sodium ampicillin was found to be excreted to the extent of about 79% after intravenous administration whereas the corresponding value for the hetacillin methoxymethyl ester was about 26%. Due to the extended half-life values for the hetacillin ester, urine and serum concentrations of the hydrolysis product ampicillin are maintained at higher levels for a longer period of time after admnistration of the hetacillin ester than after administration of ampicillin itself. The rate and extent of oral absorption of the methoxymethyl ester of hetacillin is significantly greater than that obtained with ampicillin trihydrate. Although peak concentrations were approximately equivalent for both drugs, the oral bioavailability for the hetacillin ester was almost three times that of the ampicillin trihydrate. Table III, below, shows data on the therapeutic activity of methoxymethyl esters of hetacillin and ampicillin in terms of the dose necessary to protect fifty percent of a mouse population challenged by exposure to a test organism. It can be seen that the ester is generally equivalent to known established antibiotics against a sensitive organism.

TABLE III

Chemotherapeutic Activity of Ampicillin, Hetacillin, and the Methoxymethyl Esters of Hetacillin and Ampicillin Following Oral Administration to Mice Infected with *Escherichia coli*

| | Compound | Vehicle | Oral PD$_{50}$ *E. coli* Test 1 | mg/kg* A15119 Test 2 |
|---|---|---|---|---|
| (1) | Ampicillin | H$_2$O | 70 | 80 |
| (2) | Hetacillin | H$_2$O | 70 | 76 |
| (3) | Hetacillin Ester | H$_2$O | 70 | 50 |
| (4) | Ampicillin Ester | H$_3$PO$_4$ Buffer | 50 | 54 |

*All compounds were administered orally at equimolar concentrations to mice at 1 hour post-challenge.
PD$_{50}$ = Protective dose, 50%.

We claim:

1. The compound of the formula

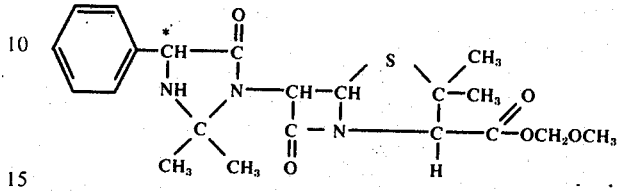

having the D$^-$ configuration at the carbon atom marked with an asterisk.

2. The hydrochloride of the compound of claim 1.